United States Patent [19]

Yamada et al.

[11] Patent Number: 4,962,242

[45] Date of Patent: Oct. 9, 1990

[54] PROCESS FOR PRODUCING OPTICALLY ACTIVE ALCOHOLS

[75] Inventors: Nobuo Yamada, Kanagawa; Toshiyuki Takezawa, Saitama; Noboru Sayo; Misao Yagi, both of Kanagawa; Hidenori Kumobayashi; Susumu Akutagawa, both of Kanagawa; Hidemasa Takaya; Shinichi Inoue, both of Aichi; Ryoji Noyori, Aichi, all of Japan

[73] Assignee: Takasago Perfumery Co., Ltd., Tokyo, Japan

[21] Appl. No.: 66,164

[22] Filed: Jun. 25, 1987

[30] Foreign Application Priority Data

Aug. 27, 1986 [JP] Japan .................. 61-200859
Mar. 25, 1987 [JP] Japan .................. 62-69056

[51] Int. Cl.$^5$ .................. C07C 29/17; C07C 31/125; C07C 31/135; C07C 33/025
[52] U.S. Cl. .................. 568/822; 502/162; 568/875; 568/903
[58] Field of Search .................. 568/903, 828, 822, 875

[56] References Cited

U.S. PATENT DOCUMENTS

| | | | |
|---|---|---|---|
| 3,849,480 | 11/1974 | Knowles et al. | 568/903 |
| 3,857,900 | 12/1974 | Wilkinson | 568/828 |
| 4,117,016 | 9/1978 | Hughes | 568/903 |
| 4,388,479 | 6/1983 | Gryaznovetal | 568/903 |
| 4,691,037 | 9/1987 | Yoshikawa et al. | 556/18 |

FOREIGN PATENT DOCUMENTS

3438851 4/1986 Fed. Rep. of Germany ...... 568/903

OTHER PUBLICATIONS

Inoue et al., "Asymmetric Hydrogenation of Geraniol, Etc.," Chemistry Letterrs, pp. 1007–1008 (1985).
Ikariya et al., "Synthesis of Novel Chiral Ruthenium Complexes, Etc.," J. Chem. Soc., Chem. Commun., pp. 922–924 (1985).
Takaya et al., "Enantioselective Hydrogenation of Allylic, Etc.," J. Amer. Chem. Soc'y, vol. 109, pp. 1596–1597 (Mar., 1987).

Journal of The Chemical Society, Chemical Communications, 1985, pp. 922–924, The Royal Chemical Society, London, GB; T. Ikariya et al.: "Synthesis of Novel Chiral Ruthenium Complexes of . . . Catalysts".
Chemistry Letters, No. 7, 1985, pp. 1007–1008, The Chemical Society of Japan, Tokyo, JP; Shin-Ichi Inoue et al: "Asymmetric Hydrogenation of Geraniol and Nerol Catalyzed by BINAP-Rhodium (I) Complexes".

*Primary Examiner*—J. E. Evans
*Attorney, Agent, or Firm*—Sughrue, Mion, Zinn, Macpeak & Seas

[57] ABSTRACT

A process for producing an optically active alcohol represented by formula (I):

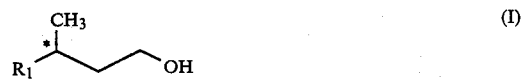

(I)

wherein $R_1$ is an alkyl group having from 2 to 11 carbon atoms, an alkenyl group having from 3 to 11 carbon atoms, an alkadienyl group having from 6 to 11 carbon atoms, a cyclohexyl group, an cyclohexylmethyl group, or a cyclohexylethyl group, provided that the olefin in the alkenyl group or alkadienyl group is not conjugated to the olefin at the 2-position thereof; and * means an asymmetric carbon atom, is disclosed, comprising subjecting an olefinic alcohol represented by formula (II):

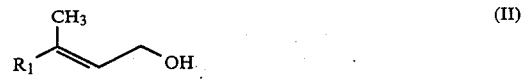

(II)

wherein $R_1$ is the same as defined above
to asymmetric hydrogenation in the presence of, as a catalyst, a ruthenium-optically active phosphine complex.

According to the process of the invention, the desired optically active alcohols which are useful not only as intermediates for the manufacture of perfumes and vitamin E but also as liquid crystal materials can be produced with high optical purities.

5 Claims, No Drawings

PROCESS FOR PRODUCING OPTICALLY ACTIVE ALCOHOLS

FIELD OF THE INVENTION

The present invention relates to a process for producing optically active alcohols by asymmetric synthesis.

BACKGROUND OF THE INVENTION

Optically active alcohols represented by formula (I):

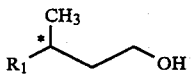
(I)

wherein $R_1$ is an alkyl group having from 2 to 11 carbon atoms, an alkenyl group having from 3 to 11 carbon atoms, an alkadienyl group having from 6 to 11 carbon atoms, a cyclohexyl group, an cyclohexylmethyl group, or a cyclohexylethyl group, provided that the olefin in the alkenyl group or alkadienyl group is not conjugated to the olefin at the 2-position thereof; and * means an asymmetric carbon atom, are useful not only as intermediates for the production of perfumes and vitamin E but also as liquid crystal materials.

Several methods of asymmetric synthesis have been available for producing such optically active alcohols, for example, (1) a method starting with naturally occurring optically active isomers; (2) a method utilizing microbial asymmetric hydrogenation; and (3) a method involving asymmetric hydrogenation in the presence of a specified catalyst. In particular, as a method for obtaining the optically active alcohol of formula (I) by asymmetric synthesis of an olefinic alcohol represented by formula (II):

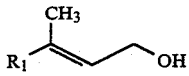
(II)

wherein $R_1$ is the same as defined above,
it is reported in *Chemistry Letters*, pp. 1007–1008 (1985) that the asymmetric synthesis is performed by asymmetric hydrogenation of geraniol or nerol in the presence of, as a catalyst, a rhodium-optically active phosphine complex.

On the other hand, as to asymmetric hydrogenation using, as a catalyst, a ruthenium complex, it is reported in *J. Chem. Soc., Chem. Commun.*, pp. 922–924 (1985) and European Pat. No. 174,057A that N-benzoylphenylalanine with an optical purity of 92% was obtained from 2-α-benzoylaminocinnamic acid and (3R)-3-methyl- or (3R)-3-phenyl-γ-valerolactone with an optical purity of 39% or 33% from 3-methyl- or 3-phenylglutaric anhydride, respectively.

Among these methods of asymmetric synthesis, according to the method (1) starting with naturally occurring optically active isomers or method (2) utilizing microbial asymmetric hydrogenation, though desired alcohols with high optical purities can be obtained, not only is the absolute configuration of the resulting optically active alcohols limited to a specific one, but also it is difficult to synthesize their enantiomers. Further, in accordance with the asymmetric hydrogenation of allyl alcohol derivatives using a rhodium-optically active phosphine catalyst, not only are the optical purities of the resulting alcohols not yet satisfactory, but also since metallic rhodium to be used is expensive due to limitations in place and quantity of production when used as a catalyst component, it forms a large proportion in cost of the catalyst, ultimately resulting in an increase in cost of the final commercial products.

SUMMARY OF THE INVENTION

In order to solve the aforesaid problems, the present inventors have conducted intensive studies and eventually found that when asymmetric hydrogenation is carried out using, as a catalyst, a relatively cheap ruthenium-optically active phosphine catalyst, the desired alcohol with a high optical purity can be obtained.

An object of the present invention is, therefore, to provide a process for producing an optically active alcohol represented by formula (I):

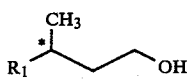
(I)

wherein $R_1$ is an alkyl group having from 2 to 11 carbon atoms, an alkenyl group having from 3 to 11 carbon atoms, an alkadienyl group having from 6 to 11 carbon atoms, a cyclohexyl group, an cyclohexylmethyl group, or a cyclohexylethyl group, provided that the olefin in the alkenyl group or alkadienyl group is not conjugated to the olefin at the 2-position thereof; and * means an asymmetric carbon atom,
which process comprises subjecting an olefinic alcohol represented by formula (II):

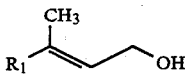
(II)

wherein $R_1$ is the same as defined above,
to asymmetric hydrogenation in the presence of, as a catalyst, a ruthenium-optically active phosphine complex.

DETAILED DESCRIPTION OF THE INVENTION

Examples of the olefinic alcohol of formula (II) which can be used as the starting material in the process of the present invention include:
(2E)-3-methyl-2-penten-1-ol;
(2E)-3,4-dimethyl-2-penten-1-ol;
(2E)-3-methyl-2-hexen-1-ol;
(2E)-3,5-dimethyl-2-hexen-1-ol;
(2E)-3-methyl-2-hepten-1-ol;
(2E)-3,6-dimethyl-2-hepten-1-ol;
(2E)-3-methyl-2-octen-1-ol;
(2E)-3,7-dimethyl-2-octen-1-ol;
(2E)-3-methyl-2-nonen-1-ol;
(2E)-3,7-dimethyl-2-nonen-1-ol
(2E)-3-methyl-2-decen-1-ol;
(2E)-3-methyl-2-undecen-1-ol;
(2E, 7R)-3,7,11-trimethyl-2-dodecen-1-ol;
(2E, 7S)-3,7,11-trimethyl-2-dodecen-1-ol;
(2Z, 7R)-3,7,11-trimethyl-2-dodecen-1-ol;
(2E)-3-methyl-2,5-hexadien-1-ol;
(2E, 5E)-3-methyl-2,5-hexadien-1-ol;

(2E)-3-methyl-2,6-heptadien-1-ol;
(2E)-3, 5-dimethyl-2,5-hexadien-1-ol;
(2E, 6E)-3-methyl-2,6-octadien-1-ol;
(2E)-3-methyl-2,7-octadien-1-ol;
(2E)-3,6-dimethyl-2,5-heptadien-1-ol;
(2E)-3,6-dimethyl-2,6-heptadien-1-ol;
(2E, 6E)-3-methyl-2,7-nonadien-1-ol;
(2E)-3-methyl-2,8-nonadien-1-ol;
geraniol;
nerol;
(2E)-3,7-dimethyl-2,7-octadien-1-ol;
(2E, 5E)-3,7-dimethyl-2,5-octadien-1-ol;
(2E, 8E)-3-methyl-2,8-decadien-1-ol;
(2E)-3-methyl-2,9-decadien-1-ol;
(2E)-3,8-dimethyl-2,7-nonadien-1-ol;
(2E)-3,6,7-trimethyl-2,6-octadien-1-ol;
(2E, 6E)-3,7-dimethyl-2,6-undecadien-1-ol;
(2E)-3,7,11-trimethyl-2,10-dodecadien-1-ol;
(2E, 5E)-3,7-dimethyl-2,5,7-octatrien-1-ol;
(2E, 6E, 10E)-3-methyl-2,6,10-dodecatrien-1-ol;
(2E, 6E)-3,7,11-trimethyl-2,6,10-dodecatrien-1-ol;
(2Z, 6E)-3,7,11-trimethyl-2,6,10-dodecatrien-1-ol;
(2E, 6Z)-3,7,11-trimethyl-2,6,10-dodecatrien-1-ol;
(2E)-3-cyclohexyl-2-buten-1-ol;
(2E)-3-methyl-4-cyclohexyl-2-buten-1-ol; and
(2E)-3-methyl-5-cyclohexyl-2-penten-1-ol.

Examples of the ruthenium-optically active phosphine complex which can be used as the catalyst in the present invention are those as described below. In the following examples, the abbreviations as designated below are used.

| | |
|---|---|
| Bu: | Butyl group |
| t-Bu: | t-Butyl group |
| i-Pr: | Isopropyl group |
| Ph: | Phenyl group |
| BINAP: | 2,2'-Bis(diphenylphosphino)-1,1'-binaphthyl |
| T-BINAP: | 2,2'-Bis(di-p-tolylphosphino)-1,1'-binaphthyl |
| t-BuBINAP: | 2,2'-Bis(di-p-t-butylphenylphosphino)-1,1'-binaphthyl |
| sulfonated BINAP: | 2,2'-Bis(diphenylphosphino)-5,5'-bis-(sodium sulfonate)-1,1'-binaphthyl |
| amino BINAP: | 2,2'-Bis(diphenylphosphino)-5,5'-bis-(amino)-1,1'-binaphthyl |
| acetylamino BINAP: | 2,2'-Bis(diphenylphosphino)-5,5'-bis-(acetylamino)-1,1'-binaphthyl |
| (1) | $Ru_xH_yCl_z(R_2\text{-BINAP})_2(S)_p$ (III) |

(1)

$$Ru_xH_yCl_z(R_2-R_2-BINAP)_2(S)_p \qquad (III)$$

wherein $R_2$—BINAP signifies a tertiary phosphine of formula
wherein $R_2$-BINAP signifies a tertiary phosphine of formula (IV):

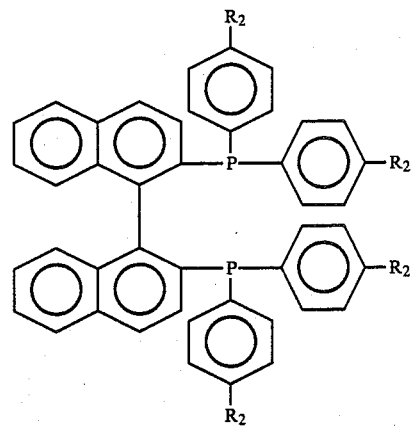

in which $R_2$ is hydrogen, a methyl group, or a t-butyl group; S is a tertiary amine; when y is 0, then x is 2, z is 4, and p is 1; and when y is 1, then x is 1, z is 1, and p is 0.

Examples of the tertiary amine for S include triethylamine, tri-n-butylamine, tri-n-octylamine, N-methylpiperidine, N-methylpyrrolidine, N-methylmorpholine, pyridine, dimethylaniline, and tetramethylethylenediamine.

The complex of formula (III) can be obtained by the methods described in J. Chem. Soc., Chem. Commun., pp. 922-924 (1985) and European Pat. No. 174,057A. That is, ruthenium chloride is reacted with cycloocta-1,5-diene (abbreviated as "COD") in an ethanol solution to form [RuCl₂(COD)]n, and one mole of this complex is reacted with (R₂-BINAP) under heating in a solvent such as toluene or ethanol in the presence of 4 moles of a tertiary amine. Specific examples of the complex of formula (III) are listed below:

Ru₂Cl₄((-)-BINAP)₂(C₂H₅)₃N;

Ru₂Cl₄((+) -T-BINAP)₂(C₂H₅)₃N;

Ru₂Cl₄((+)-t-BuBINAP)₂(C₂H₅)₃N;

RuHCl((-)-BINAP)₂;

Ru₂Cl₄((+)-BINAP)₂Bu₃N; and

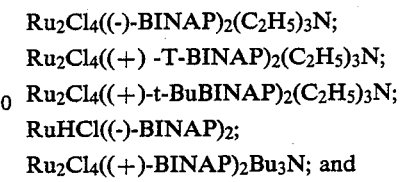

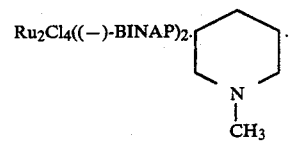

wherein X-R₃-BINAP signifies a tertiary phosphine of formula (VI):

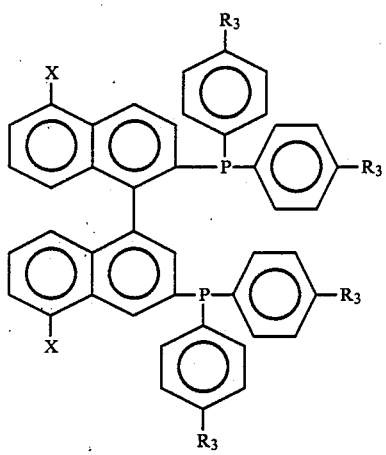

(VI)

X represents a hydrogen atom, an amino group, an acetylamino group, or a sulfo group; $R_3$ represents a hydrogen atom or a lower alkyl group (e.g., those having from 1 to 4 carbon atoms); $R_4$ and $R_5$ each represents an alkyl group (e.g., those having from 1 to 9 carbon atoms), a halogenated lower alkyl group (e.g., those having from 1 to 4 carbon atoms; examples of the halogen include fluoride, chlorine, and bromine), a phenyl group, a phenyl group substituted with a lower alkyl group (e.g., those having from 1 to 4 carbon atoms), an α-aminoalkyl group (e.g., those having from 1 to 4 carbon atoms), or an α-aminophenylalkyl group (e.g., those having from 7 to 10 carbon atoms), or $R_4$ and $R_5$ are taken together to form an alkylene group (e.g., those having from 1 to 4 carbon atoms); and q represents 1 or 2.

The complex of formula (V) can be prepared in accordance with the method as disclosed in Japanese Pat. application Ser. No. 108888/1986 (corresponding to U.S. application Ser. No. 38,570, filed April 15, 1987). That is, $RuCl_4(X-R_3-BINAP)_2(NEt_3)$ (wherein $NEt_3$ signifies triethylamine) as a starting material is reacted with a carboxylic acid salt in an alcoholic solvent such as methanol, ethanol, or t-butanol at a temperature of from about 20° to 110° C. for a period of time of from 3 to 15 hours; after distilling off the solvent, the desired complex is extracted with a solvent such as diethyl ether or ethanol; and the extract is evaporated to dryness to obtain a crude complex which is then recrystallized from a suitable solvent such as ethyl acetate, whereby a purified product can be obtained.

If an optically active form of $X-R_3-BINAP$ is used in the method described above, a ruthenium-phosphine complex of formula (V) having corresponding optically active properties can be obtained.

Specific examples of the complex of formula (V) are listed below:

$Ru(BINAP)(O_2CCH_3)_2$;
$Ru(BINAP)(O_2CCF_3)_2$;
$Ru(T-BINAP)_2(O_2CCH_3)_2$;
$Ru(BINAP)(O_2Ct-Bu)_2$;
$Ru(BINAP)(O_2CPh)_2$;
$Ru(T-BINAP)(O_2CCH_3)_2$;

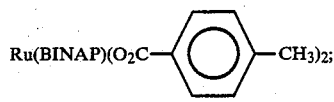

$Ru(T-BINAP)(O_2CCF_3)_2$;
$Ru(t-BuBINAP)(O_2CCH_3)_2$;
$Ru(amino\ BINAP)(O_2CCH_3)_2$;
$Ru(acetylamino\ BINAP)(O_2CCH_3)_2$;
$Ru(sulfonated\ BINAP)(O_2CCH_3)_2$;

$Ru(BINAP)(OC(CH_2)_3CO)$;
         $\overset{\|}{O}$      $\overset{\|}{O}$ $Ru(T-BINAP)_2(O_2CCF_3)_2$;

$Ru(BINAP)(O_2CCHCH_2Ph)_2$; and  (VII)
              |
              $NH_2$ $Ru(BINAP)(O_2CCH-i-Pr)_2$.
              |
              $NH_2$ (3)  $[RuH_l(R_6-BINAP)_v]Y_w$ wherein $R_6$-BINAP signifies a tertiary phosphine of formula (VIII):

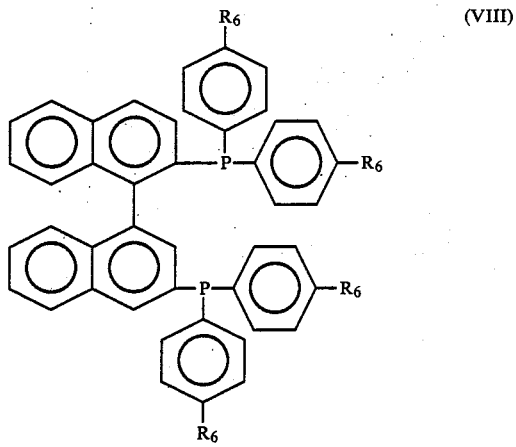

(VIII)

$R_6$ is hydrogen or a methyl group; Y is $ClO_4$, $BF_4$, or $PF_6$; when l is 0, then v is 1 and w is 2; and when l is 1, then v is 2 and w is 1.

A complex of formula (VII) wherein l is 0, v is 1, and w is 2 is produced by reacting, as a starting compound, - $Ru_2Cl_4(R_6-BINAP)_2(NEt_3)$ with a salt represented by formula (IX):

MY  (IX)

wherein M is a metal selected from the group consisting of Na, K, Li, Mg, and Ag; and Y is $ClO_4$, $BF_4$, or $PF_6$, in a solvent composed of water and methylene chloride in the presence of, as a phase transfer catalyst, a quaternary ammonium salt or a quaternary phosphonium salt represented by formula (X):

$R_7R_8R_9R_{10}AB$  (X)

wherein $R_7$, $R_8$, $R_9$, and $R_{10}$ are each an alkyl group having from 1 to 16 carbon atoms, a phenyl group, or a benzyl group; A is nitrogen or phosphorus; and B is a halogen.

The reaction between $Ru_2Cl_4(R_6\text{-BINAP})_2(NEt_3)$ and the salt of formula (IX) is carried out by adding these two compounds and the phase transfer catalyst of formula (X) in a mixed solvent of water and methylene chloride and stirring the mixture. The salt of formula (IX) is used in an amount of from 2 to 10 moles and preferably 5 moles per mole of the ruthenium, and the phase transfer catalyst of formula (X) is used in an amount of from 1/100 to 1/10 mole per mole of the ruthenium, respectively. It suffices to continue the stirring for a period of time of from 6 to 18 hours and typically 12 hours at a temperature of from 5° to 30° C.

Examples of the salt of formula (IX) include perchlorates, borofluorides, and hexafluorophosphates of Na, K, Li, Mg, or Ag. Compounds useful as the phase transfer catalyst of formula (X) are found in documented references, such as W. P. Weber and G. W. Gokel, *Phase Transfer Catalysis in Organic Synthesis*, Springer-Verlag, pp. 6 (1977).

After completion of the reaction, the reaction mixture is allowed to stand, and the methylene chloride solution separated from the aqueous layer is washed and stripped of the methylene chloride by evaporation under vacuum so as to obtain the end product.

Alternatively, the end compound can be synthesized by reacting $Ru(R_6\text{-BINAP})(O_2CCH_3)_2$ (a compound of formula (V) wherein X is H; $R_3$ is H or methyl; and $R_4$ and $R_5$ are each methyl) with an acid represented by formula (XI):

HY        (XI)

wherein Y is $ClO_4$, $BF_4$, or $PF_6$, under stirring in a mixed solvent of methylene chloride and methanol. The acid of formula (XI) is used in an amount of from 2 to 6 moles and preferably 4 moles per mole of the ruthenium. It suffices to continue the stirring for a period of time of from 6 to 18 hours and typically 12 hours at a temperature of from 5° to 30° C.

A compound of formula (VII) wherein l is 1, v is 2, and w is 1 can be produced by reaction of, as a starting material, $RuHCl(R_6\text{-BINAP})_2$ with the salt of formula (IX) in a mixed solvent of water and methylene chloride in the presence of the phase transfer catalyst of formula (X). The salt of formula (IX) is used in an amount of from 2 to 10 moles and preferably 5 moles per mole of the ruthenium, and the phase transfer catalyst of formula (X) is used in an amount of from 1/100 to 1/10 mole per mole of the ruthenium. It suffices to continue the stirring for a period of time of from 6 to 18 hours and typically 12 hours at a temperature of from 5° to 30° C.

Specific examples of the complex of formula (VII) are listed below:
[Ru(T-BINAP)]($BF_4$)$_2$;
[RuH(T-BINAP)$_2$]$BF_4$;
[Ru(BINAP)]($BF_4$)$_2$;
[Ru(BINAP)]($ClO_4$)$_2$;
[Ru(T-BINAP)]($ClO_4$)$_2$;
[Ru(T-BINAP)]($PF_6$)$_2$;
[RuH(BINAP)$_2$]$BF_4$;
[RuH(T-BINAP)$_2$]$ClO_4$; and
[RuH(T-BINAP)$_2$]$PF_6$.

The process of the present invention can be proceeded as follows: That is, an olefinic alcohol of formula (II) is dissolved in a protic solvent such as methanol, ethanol, or methyl cellosolve, which is used either independently or in admixture with some other suitable solvent such as tetrahydrofuran, toluene, benzene, or methylene chloride; the resulting solution is charged into an autoclave which is then fed with a ruthenium-optically active phosphine complex in an amount ranging from 1/100 to 1/50,000 mole per mole of the olefinic alcohol; the mixture is subjected to hydrogenation at a hydrogen pressure of from 5 to 100 kg/cm² and preferably from 10 to 40 kg/cm² and at a hydrogenation temperature of from 5° to 50° C. and preferably from 10 to 25° C., with agitation conducted for a period of time of from 1 to 15 hours; and after completion of the reaction, the solvent is distilled off, and the residue is distilled to obtain the desired optically active alcohol of formula (I) in a substantially quantitative yield.

The present invention is hereunder described in greater detail by way of Referential Examples and Examples which, however, should not be taken as limiting. Analyses were conducted in the Examples with the following instruments:

Gas chromatography: Shimadzu GC-9A (made by Shimadzu Seisakusho, Ltd.)
Column: OV-101 silica capillary (0.25 mm$\phi$×25 m$^L$, made by Gasukuro Kogyo Inc.), with the temperature being increased from 100° to 250° C. at a rate of 3° C./min
High-performance liquid chromatography: Hitachi Liquid Chromatograph 655A-11 (made by Hitachi, Ltd.)
Column: Chemcopack NucleoSil 100-3 (4.6 mm$\phi$×300 mm$^L$, made by Chemco Co., Ltd.)
Solvent: hexane/diethyl ether (7:3 by volume) at a flow rate 1 ml/min
Detector: UV Detector 635M (UV-254) (made by Hitachi, Ltd.)
$^1$H NMR spectrometer: Model JNM-GX400 (400MHz) (made by
JEOL Ltd.)
Internal standard: tetramethylsilane
Polarimeter: Polarimeter DIP-4 (made by Japan Spectroscopic Co., Ltd.)
Infrared spectrometer: Infrared spectrometer IR-810 (made by Japan Spectroscopic Co., Ltd.)
$^{31}$P NMR spectrometer: Model JNM-GX400 (161 MHZ) (made by JEOL Ltd.), with chemical shifts being determined with 85% phosphoric acid used as an external standard

REFERENTIAL EXAMPLE 1

Preparation of $Ru_2Cl_4((+)\text{-T-BINAP})_2NEt_3$:

One gram (3.56 mmoles) of $[RuCl_2(COD)]_n$, 2.9 g (4.27 mmoles) of (+)-T-BINAP, and 1.5 g of triethylamine were added to 50 ml of toluene in a nitrogen atmosphere. The mixture was heated with stirring under toluene refluxing. Six hours later, the reaction mixture was cooled, and the resulting crystal was recovered by filtration. The separated crystal was dissolved in toluene, and recrystallization was effected by gradual addition of diethyl ether. As a result, a purified crystal was obtained in an amount of 2.24 g.

This complex had the following data of elemental analysis except for Ru:

| | C | H | N | Cl |
|---|---|---|---|---|
| Found (%): | 66.4 | 5.3 | 0.73 | 10.5 |
| Calculated (%): | 67.9 | 5.3 | 0.78 | 7.9 |

REFERENTIAL EXAMPLE 2

Preparation of Ru$_2$Cl$_4$((−)-T-BINAP)$_2$NEt$_3$:

The titled compound was synthesized in the same manner as in Referential Example 1 except that the (+)-T-BINAP was replaced by (−)-T-BINAP.

REFERENTIAL EXAMPLE 3

Preparation of RuHCl((−)-T-BINAP)$_2$:

One gram (3.56 mmoles) of [RuCl$_2$(COD)]$_n$, 5.43 g (8 mmoles) of (−)-T-BINAP, 1.6 g of triethylamine were added to 100 ml of ethanol in a reactor. The contents of the reactor were heated under reflux for 6 hours with stirring in a nitrogen atmosphere. After completion of the reaction, the ethanol was distilled off, and the residue was dissolved in 40 ml of dichloromethane, with the insoluble matter being filtered off. The filtrate was recrystallized by gradual addition of diethyl ether. Upon vacuum drying, a purified crystal was obtained in an amount of 3.4 g.

REFERENTIAL EXAMPLE 4

Preparation of Ru((−)-T-BINAP)$_2$(O$_2$CCH$_3$)$_2$:

A Schlenk-tube was charged with 0.45 g (0.3 mmole) of RuHCl((−)-T-BINAP)$_2$ as prepared in Referential Example 3 and 0.11 g (0.66 mmole) of silver acetate. Disoxidated methylene chloride (5 ml) was added thereto, and the mixture was stirred for 12 hours at room temperature. After completion of the reaction, the reaction mixture was filtered through Celite (a trademark for a diatomaceous earth filter medium) in a nitrogen gas streatm, and the filtrate was concentrated by evaporation to dryness to obtain a crude complex in an amount of 0.57 g. The complex was dissolved in 1 ml of toluene, and 5 ml of hexane was gradually added thereto. The deposited solid was recovered by filtration in a nitrogen stream and dried at a reduced pressure (0.5 mmHg) at room tempereture to obtain a purified complex in an amount of 0.246 g (yield: 52%). The results of elemental analysis and NMR analyses showed that the purified complex was Ru((−)-T-BINAP)$_2$(O$_2$CCH$_3$)$_2$.

Elemental analysis for C$_{100}$H$_{86}$O$_4$P$_4$Ru:

| | Ru | P | C | H |
|---|---|---|---|---|
| Found (%): | 6.30 | 7.53 | 76.85 | 5.57 |
| Calculated (%): | 6.41 | 7.86 | 76.18 | 5.50 |
| $^{31}$P NMR (CDCL$_3$) δ ppm: | 63.79 | | | |

$^{31}$P NMR (CDCl$_3$)δ ppm: 63.79

$^1$H NMR (CDCL$_3$) δ ppm: 1.94

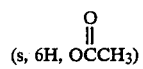
(s, 6H, OCCH$_3$)

2,34, 2.38 (s, 12H and CH$_3$ for each) 6.2 to 7.8 (m, 56H)

REFERENTIAL EXAMPLE 5

Preparation of [Ru((+)-T-BINAP)](ClO$_4$)$_2$:

A 250-ml Schlenk-tube was charged with 0.54 g (0.3 mmole) of the Ru$_2$Cl$_4$((+)-T-BINAP)$_2$NEt$_3$ as prepared in Referential Example 1. After the atmosphere in the tube had been thoroughly displaced with nitrogen, 60 ml of methylene chloride was added thereto, followed by addition of 0.73 g (6.0 mmoles) of sodium perchlorate in 60 ml of water and 16 mg (0.06 mmole) of triethylbenzylammonium bromide in 3 ml of water. Reaction was performed by stirring the contents for 12 hours at room temperature. After completion of the reaction, the reaction mixture was allowed to stand, and the methylene chloride solution separated from the aqueous layer was washed with 50 ml of water. After liquid separation, the methylene chloride was distilled off under vacuum, and the residue was vacuum-dried to obtain a dark brown solid of [Ru((+)-T-BINAP)](ClO$_4$)$_2$ in an amount of 0.59 g (yield: 99.6%).

The results of elemental analysis and $^{31}$P NMR analysis showed that the complex was [Ru((+)-T-BINAP)](ClO$_4$)$_2$.

Elemental analysis for C$_{48}$H$_{40}$Cl$_2$O$_8$P$_2$Ru:

| | Ru | P | C | H |
|---|---|---|---|---|
| Found (%): | 10.08 | 5.97 | 58.61 | 4.53 |
| Calculated (%): | 10.32 | 6.33 | 58.90 | 4.12 |
| $^{31}$P NMR (CDCl$_3$) δ ppm: | 12.920 (d, J = 41.1 Hz) | | | |
| | 61.402 (d, J = 41.1 Hz) | | | |

REFERENTIAL EXAMPLE 6

Preparation of [Ru((−)-T-BINAP)](BF$_4$)$_2$:

A 250-ml Schlenk-tube was charged with 0.54 g (0.3 mmole) of the RuCl$_4$((−)-T-BINAP)$_2$NEt$_3$ as prepared in Referential Example 2. After the atmosphere in the tube had been thoroughly displaced with nitrogen, 60 ml of methylene chloride was added thereto, followed by addition of 0.66 g (6.0 mmoles) of sodium tetrafluoroborate in 60 ml of water and 16 mg (0.06 mmole) of triethylbenzylammonium bromide in 3 ml of water. Reaction was performed by stirring the contents for 12 hours at room temperature. After completion of the reaction, the reaction mixture was allowed to stand, and the methylene chloride solution separated from the aqueous layer was washed with 50 ml of water. After liquid separation, the methylene chloride was distilled off under vacuum, and the residue was vacuum-dried to obtain a dark brown solid of [Ru((−)-T-BINAP)](BF$_4$)$_2$ in an amount of 0.55 g (yield: 95.8%).

Elemental analysis for C$_{48}$H$_{40}$B$_2$F$_8$P$_2$Ru:

| | Ru | P | C | H |
|---|---|---|---|---|
| Found (%): | 10.18 | 6.31 | 60.21 | 4.39 |
| Calculated (%): | 10.60 | 6.50 | 60.47 | 4.23 |
| $^{31}$P NMR (CDCl$_3$) δ ppm: | 12.823 (d, J = 41.1 Hz) | | | |
| | 61.390 (d, J = 41.0 Hz) | | | |

EXAMPLE 1

Synthesis of (3R)-(+)-3-Methylpentanol:

A nitrogen-purged 200-ml stainless steel autoclave was charged with 20 g (0.2 mole) of (2E)-3-methyl-2- penten-1-ol and 40 ml of methanol. Thereafter, 18 mg (0.02 mmole) of the

Ru((−)-T-BINAP)$_2$(OCCH$_3$)$_2$ as prepared in Referential Example 4 was added thereto, and hydrogenation was conducted at a hydrogen pressure of 30 kg/cm$^2$ and at a reaction temperature of 20° C. for 15 hours. The solvent was distilled off to obtain 3-methylpentanol in an amount of 20 g (yield: 100%).

b.p.: 72° C./25 mmHg.

$^1$H NMR: ($\delta$) 0.6 to 2.2 (m, 12H), 3.67 (t, 2H).

Gas chromatography showed that the product had a purity of 100% and a specific rotation $[\alpha]_D^{25}$ of $+8.5°$ (c=15.0, chloroform).

The resulting alcohol was converted to 3-methylvaleric acid by Jones' oxidation, which was then reacted with (R)-(+)-1-(1-naphthyl)ethylamine to synthesize its amide form. Diastereomeric separation and analysis by high-performance liquid chromatography showed that the starting alcohol was a mixture of 96.5% (3R)-(+)-3-methylpentanol and 3.5% (3S)-(−)-3-methylpentanol, indicating that the optical yield of (3R)-3-methylpentanol was 93% ee.

EXAMPLE 2

Synthesis of (3R)-(+)-Citronellol:

A nitrogen-purged 200-ml autoclave was charged with 30.8 g (0.2 mole) of geraniol and 50 ml of methanol. To the solution, 18 mg (0.02 mmole) of the Ru((−)-T-added,

BINAP)$_2$(OCCH$_3$)$_2$ as prepared in Referential Example 4 was and hydrogenation was conducted at a hydrogen pressure of 50 kg/cm$^2$ and at a reaction temperature of 15° C. for 20 hours with stirring. When it was confirmed that hydrogen had been absorbed in a molar amount equal to that of geraniol, the solvent was distilled off, and the residue was subjected to vacuum distillation to obtain 31 g of a (3R)-(+)-citronellol fraction having a boiling point of 80 to 83° C./1 mmHg. The yield of this fraction was 100%. Analysis by gas chromatography showed that the fraction had a purity of 96.0%.

$[\alpha]_D^{25} = +5.2°$ (c=28.4, chloroform).

$^1$H NMR: ($\delta$)0.9(d, 3H), 1.0 to 2.4 (m, 16H), 3.6 (t, 2H), 5.1 (t, $^1$H).

The fraction was converted to a corresponding amide in the same manner as in Example 1, and analysis showed that the optical yield of the end compound was 96% ee.

EXAMPLE 3

Synthesis of (3R)-(+)-Citronellol:

A nitrogen-purged 200-ml autoclave was charged with 30.8 g (0.2 mole) of nerol and 60 ml of methanol. To the solution, 9.78 mg (0.01 mole) of the [Ru((+)-T-BINAP)](ClO$_4$)$_2$ as prepared in Referential Example 5 was added, and hydrogenation was conducted at a hydrogen pressure of 30 kg/cm$^2$ and at a reaction temperature of 10° C. for 15 hours. When it was confirmed that 0.2 mole of hydrogen had been absorbed, the solvent was distilled off, and the residue was subjected to vacuum distillation to obtain 30.8 g of a (3R)-(+)-citronellol fraction having a boiling point of 81 to 85° C./1 mmHg. The yield of this fraction was 100%. Analysis by gas chromatography showed that the fraction had a purity of 97%.

$[\alpha]_D^{25} = +5.2°$ (c=20.1, chloroform).

The fraction was converted to a corresponding amide in the same manner as in Example 1, and analysis showed that the optical yield of the end compound was 97% ee.

EXAMPLE 4

Synthesis of (3S)-(−)-Citronellol:

A nitrogen-purged 500-ml autoclave was charged with 30.8 g (0.2 mole) of geraniol and 70 ml of ethanol. To the solution, 32.36 mg (0.02 mole) of the Ru$_2$Cl$_4$-((+)-T-BINAP)$_2$NEt$_3$ as prepared in Referential Example 1 was added, and hydrogenation was conducted at a hydrogen pressure of 70 kg/cm$^2$ and at a reaction temperature of 20° C. for 8 hours. When it was confirmed that 0.2 mole of hydrogen had been absorbed, the solvent was distilled off, and the residue was subjected to vacuum distillation to obtain 30.8 g of a (3S)-(−)-citronellol fraction having a boiling point of 80 to 86° C./1 mmHg. The yield of this fraction was 100%. Analysis by gas chromatography showed that the fraction had a purity of 98.4%.

$[\alpha]_D^{25} = -5.2°$ (c=19.7, chloroform).

The fraction was converted to a corresponding amide in the same manner as in Example 1, and analysis showed that the optical yield of the end compound was 93% ee.

EXAMPLE 5

Synthesis of (+)-(3R, 7R)-3,7,11-Trimethyldodecanol:

A nitrogen-purged 300-ml autoclave was charged with 22.6 g (0.1 mmole) of (2E, 7R)-3,7,11-trimethy-2-dodecen-1-ol and 60 ml of methanol. To the solution, 8.97 mg (0.01 mmole) of the

Ru((−)-T-BINAP)$_2$(OCCH$_3$)$_2$ as prepared in Referential Example 4 was added, and hydrogenation was conducted at a hydrogen pressure of 30 kg/cm$^2$ and at a reaction temperature of 20° C. for 10 hours. When it was confirmed that 0.1 mole of hydrogen had been absorbed, the solvent was distilled off, and the residue was subjected to vacuum distillation to obtain 22 g of a (+)-(3R, 7R)-3,7,11-trimethyldodecanol having a boiling point of 114 to 117° C./0.25 mmHg. The yield of this fraction was 97.3%. Analysis by gas chromatography showed that the fraction had a purity of 99.2%.

$[\alpha_D^{25} = +3.4°$ (c=18, chloroform).

$^1$H NMR: ($\delta$) 0.83 to 0.91 (m, 12H), 1.01 to 1.69 (m, 18H), 3.62 to 3.73 (m, 2H).

The fraction was converted to a corresponding amide in the same manner as in Example 1, and analysis showed that the optical yield of the end compound was 98% ee.

EXAMPLE 6

Synthesis of (+)-(6E)-3,7,11-Trimethyl-6,10-dodecadien1-ol:

A nitrogen-purged 200-ml autoclave was charged with 22.1 g (0.1 mole) of (2E, 6E)-3,7,11-trimethyl2,6,10-dodecatrien-1-ol and 40 ml of methanol. To the solution, 4.8 mg (0.005 mmole) of the [Ru((−)-T-BINAP)](BF$_4$)$_2$ as prepared in Referential Example 6 was added, and hydrogenation was conducted at a hydrogen pressure of 30 kg/cm$^2$ and at a reaction temperature of 20° C. for 10 hours. When it was confirmed that 0.1 mole of hydrogen had been absorbed, the solvent methanol was distilled off, and the residue was subjected to vacuum distillation to obtain 22 g of a (+)-(6E)-3,7,11- trimethyl-6,10-dodecadien-1-ol having a boiling point of 115 to 118° C./0.2 mmHg. The yield of this fraction was 99.5%.

$^1$H NMR: (δ) 0.91 (d, 3H), 1.39 (m, 4H), 1.5 to 1.8 (m, 11H), 1.9 to 2.1 (m, 6H), 3.68 (m, 2H), 5.10 (m, 2H).

[α]$_D^{25}$ = +4.1° (c=20, chloroform).

IR spectrum: 3320, 2950, 2900, 1440, 1370 (cm$^{-1}$).

The fraction was converted to a corresponding amide in the same manner as in Example 1, and analysis showed that the optical yield of the end compound was 93% ee.

EXAMPLES 7 TO 13

Asymmetric hydrogenation of olefinic alcohols was conducted in the same manner as in Examples 1 to 6, and the results are shown in Table 1 wherein the parenthesized figures under boiling points (b.p.) show the pressure for distillation in mmHg.

tion find extensive utilities not only as intermediates for the manufacture of perfumes and vitamin E but also as liquid crystal materials.

While the invention has been described in detail and with reference to specific embodiments thereof, it will be apparent to one skilled in the art that various changes and modifications can be made therein without departing from the spirit and scope thereof.

What is claimed is:

1. A process for producing an optically active alcohol represented by formula (I):

wherein R$_1$ is an alkyl group having from 2 to 11 carbon atoms, an alkenyl group having from 3 to 11 carbon atoms, an alkadienyl group having from 6 to 11 carbon atoms, a cyclohexyl group, a cyclohexylmethyl group, or a cyclohexylethyl group, provided that the olefin in the alkenyl group or alkadienyl group is not conjugated to the olefin at the 2-position thereof; and * means an asymmetric carbon atom, which process comprises subjecting an olefinic alcohol represented by formula (II):

wherein R$_1$ is the same as defined above, to asymmetric hydrogenation in the presence of, as a

TABLE 1

| Example No. | Starting Alcohol | Catalyst | Product | b.p. | [α]$_D^{25}$ | Optical Yield (% ee) |
|---|---|---|---|---|---|---|
| 7 | [structure] | Ru((−)-T-BINAP) (BF$_4$)$_2$ | [structure] | 164° C. (760) | +27.1 (neat) | 98 |
| 8 | [structure] | Ru((−)-BINAP) (O$_2$CCH$_3$)$_2$ | [structure] | 88 (3) | +3.50 (neat) | 92 |
| 9 | [structure] | Ru((−)-T-BINAP) (ClO$_4$)$_2$ | [structure] | 102–104 (12) | +4.30 (neat) | 96 |
| 10 | [structure] | Ru((+)-BINAP) (CF$_3$CO$_2$)$_2$ | [structure] | 117 (2) | −4.10 (neat) | 95 |
| 11 | [structure] | Ru((+)-BINAP) (BF$_4$)$_2$ | [structure] | 80 (2) | −2.50 (neat) | 95 |
| 12 | [structure] | Ru((−)-T-BINAP) (CF$_3$CO$_2$)$_2$ | [structure] | 134 (24) | +6.20 (neat) | 97 |
| 13 | [structure] | RuHCl((+)-BINAP)$_2$ | [structure] | 120 (1) | −10.65 (neat) | 98 |

According to the present invention, optically active alcohols can be produced in an industrially advantageous manner by performing asymmetric hydrogenation on olefinic alcohols in the presence of, as a catalyst, a ruthenium-optically active phosphine complex. The optically active alcohols produced by the present invention catalyst, a ruthenium-optically active phosphine complex, said ruthenium-optically active phosphine complex being one represented by formula (v):

$$(Ru(X-R_3-BINAP)_q](OCR_4)(OCR_5) \quad (V)$$
$$\begin{array}{cc} \| & \| \\ O & O \end{array}$$

wherein S-R-hd 3-BINAP signifies a tertiary phosphine of formula (VI):

(VI)

[Structure: binaphthyl with X substituents and two P(C₆H₄-R₃)₂ groups]

wherein X represents a hydrogen atom, an amino group, an acetylamino group, or a sulfo group; $R_3$ represents a hydrogen atom or a lower alkyl group; $R_4$ and $R_5$ each represents an alkyl group, a halogenated lower alkyl group, a phenyl group, a phenyl group substituted with a lower alkyl group, an α-aminoalkyl group, or an α-aminophenylalkyl group, or $R_4$ and $R_5$ are taken together to form an alkylene group; and q represents 1 or 2.

2. A process a sin claim 1, wherein the lower alkyl group is an alkyl group having from 1 to 4 carbon atoms; the alkyl group is an alkyl group having from 1 to 9 carbon atoms; the alkyl group in the α-aminoalkyl group is an alkyl group having from 1 to 4 carbon atoms; and the alkyl group in the α-aminophenylalkyl group is an alkyl group having from 1 to 4 carbon atoms.

3. A process as in claim 1, wherein said ruthenium-optically active phosphine complex is selected from among the following:
Ru(BINAP)(O₂CCH₃)₂;
Ru(BINAP)(O₂CCF₃)₂;
Ru(T-BINAP)₂(O₂CCH₃)₂;
Ru(BINAP)(O₂Ct-Bu)₂;
Ru(BINAP)(O₂CPh)₂;
Ru(t-BINAP)(O₂CCH₃)₂;

Ru(BINAP)(O₂C—C₆H₄—CH₃)₂;

Ru(T-BINAP)(O₂CCF₃)₂;
Ru(t-BuBINAP)(O₂CCH₃)₂;
Ru(amino BINAP)(O₂CCH₃)₂;
Ru(acetylamino BINAP)(O₂CCH₃)₂;
Ru(sulfonated BINAP)(O₂CCH₃)₂;

$$Ru(BINAP)(OC(CH_2)_3CO);$$
$$\begin{array}{cc} \| & \| \\ O & O \end{array}$$

Ru(T-BINAP)₂(O₂CCF₃)₂;

Ru(BINAP)(O₂CCHCH₂Ph)₂; and
            |
            NH₂

Ru(BINAP)(O₂CCH-i-Pr)₂,
            |
            NH₂ wherein i-Pr signifies an isopropyl group; Ph signifies a phenyl group; BINAP signifies 2,2'-bis(diphenylphosphino)-1,1'-binaphthyl; T-BINAP signifies 2,2'-bis(di-p-tolyl-phosphino)-1,1'-binaphthyl; t-BuBINAP signifies 2,2'-bis-(di-p-t-butylphenylphosphino)-1,1'-binaphthyl; sulfonated BINAP signifies 2,2'-bis(diphenylphosphino)-5,5'-bis-(sodium sulfonate)-1,1'-naphthyl; amino BINAP signifies 2,2'-bis(diphenylphosphino)-5,5'-bis-(amino)-1,1'-bi-naphthyl; and acetylamino BINAP signifies 2,2'-bis(diphenylphosphino)-5,5'-bis-(acetylamino)-1,1-binaphthyl.

4. A process for producing an optically active alcohol represented by formula (I):

$$\underset{R_1}{\overset{CH_3}{\underset{*}{\bigwedge}}}\!\!\!\sim\!\!\text{OH} \quad (I)$$

wherein $R_1$ is an alkyl group having from 2 to 11 carbon atoms, an alkenyl group having from 3 to 11 carbon atoms, an alkadienyl group having from 6 to 11 carbon atoms, a cyclohexyl group, a cyclohexylmethyl group, or a cyclohexylethyl group, provided that the olefin in the alkenyl group or alkadienyl group is not conjugated to the olefin at the 2-position thereof; and * means an asymmetric carbon atom, which process comprises subjecting an olefinic alcohol represented by formula (II):

$$\underset{R_1}{\overset{CH_3}{\bigwedge}}\!\!\!\sim\!\!\text{OH} \quad (II)$$

wherein $R_1$ is the same as defined above,
to asymmetric hydrogenation in the presence of, as a catalyst, a ruthenium-optically active phosphine complex, said ruthenium-optically active phosphine complex being one represented by formula (VII):

$$[RuHl(R_6\text{-BINAP})_v]Y_w \quad (VII)$$

wherein $R_6$-BINAP signifies a tertiary phosphine of formula (VIII):

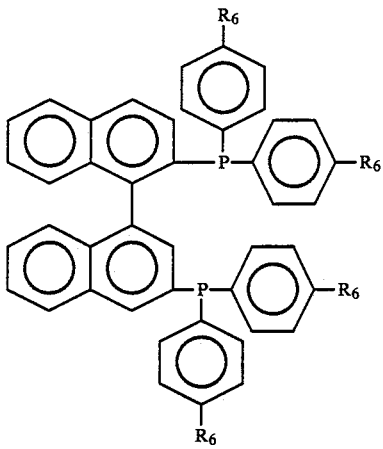
(VIII)

wherein $R_6$ is hydrogen or a methyl group; Y is $ClO_4$, $BF_4$ or $PF_6$; when l is 0, then v is 1 and w is 2; and when l is 1, then v is 2 w is 1.

5. A process as in claim 4, wherein said ruthenium-optically active phosphine complex is selected from among the following:

[Ru(T-BINAP)]($BF_4$)$_2$;
[RuH(T-BINAP)$_2$]$BF_4$;
[Ru(BINAP)]($BF_4$)$_2$;
[Ru(BINAP)]($ClO_4$)$_2$;
[Ru(T-BINAP)]($ClO_4$)$_2$;
[Ru(T-BINAP)]($PF_6$)$_2$;
[RuH(BINAP)$_2$]$BF_4$;
[RuH(T-BINAP)$_2$]$ClO_4$; and
[RuH(T-BINAP)$_2$]$PF_6$, wherein BINAP signifies 2,2'-bis(diphenylphosphino)-1,1'-binaphthyl, and T-BINAP signifies 2,2'-bis(di-p-tolyl-phosphino)-1,1'-binaphthyl.

* * * * *